(12) United States Patent
Engman et al.

(10) Patent No.: US 11,334,826 B2
(45) Date of Patent: May 17, 2022

(54) WCD SYSTEM PRIORITIZATION OF ALERTS BASED ON SEVERITY AND/OR REQUIRED TIMELINESS OF USER RESPONSE

(71) Applicant: West Affum Holdings Corp., Grand Cayman (KY)

(72) Inventors: Zoie R. Engman, Kirkland, WA (US); Pamela F. Breske, Newcastle, WA (US); David P. Finch, Bothell, WA (US); Erick M. Roane, Kirkland, WA (US)

(73) Assignee: West Affum Holdings Corp., Grand Cayman (KY)

( * ) Notice: Subject to any disclaimer, the term of this patent is extended or adjusted under 35 U.S.C. 154(b) by 0 days.

(21) Appl. No.: 16/748,621

(22) Filed: Jan. 21, 2020

(65) Prior Publication Data

US 2020/0230428 A1 Jul. 23, 2020
US 2021/0370079 A9 Dec. 2, 2021

Related U.S. Application Data

(60) Provisional application No. 62/794,335, filed on Jan. 18, 2019.

(51) Int. Cl.
*A61N 1/39* (2006.01)
*G06Q 10/06* (2012.01)
(Continued)

(52) U.S. Cl.
CPC ..... *G06Q 10/06315* (2013.01); *A61N 1/3904* (2017.08); *A61N 1/3925* (2013.01);
(Continued)

(58) Field of Classification Search
CPC ... A61N 1/3904; A61N 1/3925; A61N 1/3968
See application file for complete search history.

(56) References Cited

U.S. PATENT DOCUMENTS 3,724,355 A 4/1973 Busch et al.
4,583,524 A 4/1986 Hutchins
(Continued)

FOREIGN PATENT DOCUMENTS

DE 2005060985 A2 6/2007
EP 2305110 A1 4/2011
(Continued)

OTHER PUBLICATIONS

Heartstart MRx and XL AED Algorithm—Application Note, Jul. 2001, Edition 2 Philips Healthcare, USA.
(Continued)

*Primary Examiner* — Eric D. Bertram
(74) *Attorney, Agent, or Firm* — Christenson O'Connor Johnson & Kindness PLLC

(57) ABSTRACT

Embodiments of this disclosure are directed to a wearable cardioverter defibrillator ("WCD") system design in which a WCD implements an alert prioritization scheme to provide the patient with feedback in an order that is less likely to cause confusion. Different conditions (e.g., device status, equipment condition, or physiologic condition) are prioritized based on an analysis of severity of the condition and timeliness of user action needed. The prioritization scheme defines what alert, if any, is presented to the user by the WCD system as a result of various conditions. Generally stated, an alert for the highest priority condition currently detected is presented to the user and maintained until that condition either changes or becomes surpassed in the prioritization scheme.

18 Claims, 6 Drawing Sheets

(51) Int. Cl.
*G06F 8/10* (2018.01)
*A61N 1/04* (2006.01)

(52) U.S. Cl.
CPC ......... *A61N 1/3968* (2013.01); *A61N 1/3975* (2013.01); *G06F 8/10* (2013.01); *A61N 1/046* (2013.01)

(56) References Cited

U.S. PATENT DOCUMENTS

| | | |
|---|---|---|
| 4,619,265 A | 10/1986 | Morgan et al. |
| 4,666,432 A | 5/1987 | McNeish et al. |
| 4,698,848 A | 10/1987 | Buckley |
| 4,928,690 A | 5/1990 | Heilman et al. |
| 4,955,381 A | 9/1990 | Way et al. |
| 5,078,134 A | 1/1992 | Heilman et al. |
| 5,228,449 A | 7/1993 | Christ et al. |
| 5,285,792 A * | 2/1994 | Sjoquist ............... A61N 1/3925 600/510 |
| 5,348,008 A | 9/1994 | Bornn et al. |
| 5,353,793 A | 10/1994 | Bornn |
| RE34,800 E | 11/1994 | Hutchins |
| 5,394,892 A | 3/1995 | Kenny et al. |
| 5,405,362 A | 4/1995 | Kramer et al. |
| 5,429,593 A | 7/1995 | Matory |
| 5,474,574 A | 12/1995 | Payne et al. |
| 5,618,208 A | 4/1997 | Crouse et al. |
| 5,662,690 A | 9/1997 | Cole et al. |
| 5,708,978 A | 1/1998 | Johnsrud |
| 5,741,306 A | 4/1998 | Glegyak et al. |
| 5,782,878 A | 7/1998 | Morgan et al. |
| 5,792,204 A | 8/1998 | Snell |
| 5,902,249 A | 5/1999 | Lyster |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,280,461 B1 | 8/2001 | Glegyak et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder et al. |
| 6,427,083 B1 | 7/2002 | Owen et al. |
| 6,437,083 B1 | 8/2002 | Brack et al. |
| 6,450,942 B1 | 9/2002 | Lapanashvili et al. |
| 6,529,875 B1 | 3/2003 | Nakajima et al. |
| 6,546,285 B1 | 4/2003 | Owen et al. |
| 6,671,545 B2 | 12/2003 | Fincke |
| 6,681,003 B2 | 1/2004 | Linder et al. |
| 6,762,917 B1 | 7/2004 | Verbiest et al. |
| 7,065,401 B2 | 6/2006 | Worden |
| 7,559,902 B2 | 7/2009 | Ting et al. |
| 7,753,759 B2 | 7/2010 | Pintor et al. |
| 7,865,238 B2 | 1/2011 | Brink |
| 7,870,761 B2 | 1/2011 | Valentine et al. |
| 7,974,689 B2 | 7/2011 | Volpe et al. |
| 8,135,462 B2 | 3/2012 | Owen et al. |
| 8,140,154 B2 | 3/2012 | Donnelly et al. |
| 8,369,944 B2 | 2/2013 | Macho et al. |
| 8,527,028 B2 | 9/2013 | Kurzweil et al. |
| 8,548,557 B2 | 10/2013 | Garstka et al. |
| 8,560,044 B2 | 10/2013 | Kurzweil et al. |
| 8,615,295 B2 | 12/2013 | Savage et al. |
| 8,644,925 B2 | 2/2014 | Volpe et al. |
| 8,676,313 B2 | 3/2014 | Volpe et al. |
| 8,706,255 B2 | 4/2014 | Phillips et al. |
| 8,742,349 B2 | 6/2014 | Urbon et al. |
| 8,897,860 B2 | 11/2014 | Volpe et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,084,583 B2 | 7/2015 | Mazar et al. |
| 9,089,685 B2 | 7/2015 | Sullivan et al. |
| 9,119,547 B2 | 9/2015 | Cazares et al. |
| 9,131,901 B2 | 9/2015 | Volpe et al. |
| 9,132,267 B2 | 9/2015 | Kaib |
| 9,265,432 B2 | 2/2016 | Warren et al. |
| 9,345,898 B2 | 5/2016 | Piha et al. |
| 9,408,548 B2 | 8/2016 | Volpe et al. |
| 9,445,719 B2 | 9/2016 | Libbus et al. |
| 9,454,219 B2 | 9/2016 | Volpe et al. |
| 9,579,020 B2 | 2/2017 | Libbus et al. |
| 9,592,403 B2 | 3/2017 | Sullivan |
| 9,598,799 B2 | 3/2017 | Shoshani et al. |
| 9,675,804 B2 | 6/2017 | Whiting et al. |
| 9,878,171 B2 | 1/2018 | Kaib |
| 9,895,105 B2 | 2/2018 | Romem |
| 9,901,741 B2 | 2/2018 | Chapman et al. |
| RE46,926 E | 7/2018 | Bly et al. |
| 10,016,613 B2 | 7/2018 | Kavounas |
| 10,076,656 B2 | 9/2018 | Dar et al. |
| 10,192,387 B2 | 1/2019 | Brinig et al. |
| 10,307,133 B2 | 6/2019 | Kaib |
| 10,463,867 B2 | 11/2019 | Kaib et al. |
| 10,589,110 B2 | 3/2020 | Oskin et al. |
| 10,599,814 B2 | 3/2020 | Landrum et al. |
| 2002/0181680 A1 | 12/2002 | Linder et al. |
| 2003/0158593 A1 | 8/2003 | Heilman et al. |
| 2005/0107833 A1 | 5/2005 | Freeman et al. |
| 2005/0107834 A1 | 5/2005 | Freeman et al. |
| 2006/0173499 A1 | 8/2006 | Hampton et al. |
| 2008/0312709 A1 | 12/2008 | Vollpe et al. |
| 2009/0005827 A1 | 1/2009 | Weintraub et al. |
| 2010/0007413 A1 | 1/2010 | Herleikson |
| 2010/0298899 A1 | 11/2010 | Donnelly et al. |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2012/0112903 A1 | 5/2012 | Kaib et al. |
| 2012/0144551 A1 | 6/2012 | Guldalian |
| 2012/0150008 A1 | 6/2012 | Kaib et al. |
| 2012/0158075 A1 | 6/2012 | Kaib et al. |
| 2012/0191476 A1 | 7/2012 | Reid et al. |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2013/0085538 A1 | 4/2013 | Volpe et al. |
| 2013/0144355 A1 | 6/2013 | Macho et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0012144 A1 | 1/2014 | Crone |
| 2014/0025131 A1 | 1/2014 | Sullivan et al. |
| 2014/0046391 A1 | 2/2014 | Cowan et al. |
| 2014/0070957 A1 | 3/2014 | Longinotti-Buitoni et al. |
| 2014/0163663 A1 | 6/2014 | Poddar et al. |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2015/0161554 A1 | 6/2015 | Sweeney et al. |
| 2015/0297135 A1 | 10/2015 | Shoshani et al. |
| 2015/0328472 A1 | 11/2015 | Sullivan et al. |
| 2016/0004831 A1 | 1/2016 | Carlson et al. |
| 2016/0076175 A1 | 3/2016 | Rock et al. |
| 2016/0076176 A1 | 3/2016 | Rock et al. |
| 2016/0082277 A1 | 3/2016 | Foshee, Jr. et al. |
| 2016/0113581 A1 | 4/2016 | Amir et al. |
| 2016/0256104 A1 | 9/2016 | Romem et al. |
| 2016/0283900 A1 | 9/2016 | Johnson et al. |
| 2016/0328529 A1* | 11/2016 | Kaib ..................... A61B 5/366 |
| 2017/0014073 A1 | 1/2017 | Shoshani et al. |
| 2017/0027469 A1 | 2/2017 | Amir et al. |
| 2017/0036066 A1 | 2/2017 | Chahine |
| 2017/0040758 A1 | 2/2017 | Amir et al. |
| 2017/0162840 A1 | 6/2017 | Pendry |
| 2017/0319862 A1 | 11/2017 | Foshee, Jr. et al. |

(56) References Cited

U.S. PATENT DOCUMENTS

| | | |
|---|---|---|
| 2017/0367591 A1 | 12/2017 | Jorgensen |
| 2018/0116537 A1 | 5/2018 | Sullivan et al. |
| 2018/0117299 A1 | 5/2018 | Gustavson et al. |
| 2018/0184933 A1 | 7/2018 | Sullivan et al. |
| 2018/0185662 A1 | 7/2018 | Foshee, Jr. et al. |
| 2018/0243578 A1 | 8/2018 | Volosin |
| 2018/0361165 A1 | 12/2018 | Jaax et al. |
| 2019/0030352 A1 | 1/2019 | Sullivan et al. |
| 2019/0076666 A1 | 3/2019 | Medema |
| 2019/0116896 A1 | 4/2019 | Armour et al. |
| 2019/0321650 A1 | 10/2019 | Raymond et al. |

FOREIGN PATENT DOCUMENTS

| | | |
|---|---|---|
| JP | 4320257 A | 3/2005 |
| JP | 5963767 A | 1/2014 |
| JP | 2014526282 A | 10/2014 |
| WO | 98/39061 A2 | 9/1998 |
| WO | 1998039061 A2 | 9/1998 |
| WO | 2011/146448 A1 | 11/2011 |
| WO | 2012/064604 A1 | 5/2012 |
| WO | 2012064604 A1 | 5/2012 |
| WO | 2012/151160 A1 | 11/2012 |
| WO | 2015/056262 A1 | 4/2015 |

OTHER PUBLICATIONS

Klein, H. U., Goldenberg, I., and Moss, A. J., "Risk Stratification for Implantable Cardioverter Defibrillator Therapy: The Role of the Wearable Cardioverter-Defibrillator, Clinical update," European Heart Journal, May 31, 2013, pp. 1-14, doi:10.1093/eurheartj/eht167, European Society of Cardiology.

Lifecor LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Pagan-Carlo, et al., "Encircling Overlapping Multipulse ShockWaveforms for Transthoracic Defibrillation," JACC Journals, Dec. 1998, vol. 32 Issue 7, p. 2065-2071.

The LifeVest Network/Patient Data Management System, Zoll, 2015, 2000503 Rev A.

Zoll, LifeVest, Proven protection from Sudden Cardiac Death, issued Mar. 27, 2018, 4 pages. Pittsburgh PA, USA.

International Search Report and Written Opinion for PCT Application No. PCT/US2015/051726, dated May 20, 2016, European Patent Office, Rijswijk, 11 pages.

Klein, H. U., Goldenberg I., & Moss, A. J., Risk Stratification for Implantable Cardioverter Defibrillator Therapy: The Role of the Wearable Cardioverter-Defibrillator, Clinical update, European Heart Jounal, May 31, 2013, pp. 1-14, doi:10.1093/eurheartj/eht167, European Society of Cardiology.

Heartstart MRx and XL AED Algorithm—Application Note, Jul. 2001, Edition 2 Phillips Healthcare, USA.

Zoll LifeVest Model 4000 Patient Manual PN 20B0047 Rev B, (C) 2009-2012.

\* cited by examiner

COMPONENTS OF SAMPLE WCD SYSTEM

Priorities of Alerts and system ready behavior while Being Worn, where (1) is the highest priority and (12) is the lowest priority.

Priorities of Alerts and system ready behavior while Being Worn, where (1) is the highest priority and (12) is the lowest priority.

WCD SYSTEM PRIORITIZATION OF ALERTS BASED ON SEVERITY AND/OR REQUIRED TIMELINESS OF USER RESPONSE

CROSS REFERENCE TO RELATED PATENT APPLICATIONS

This patent application claims priority from and priority to U.S. Provisional Patent Application Ser. No. 62/794,335, filed on Jan. 18, 2019, the disclosure of which is hereby incorporated by reference for all purposes.

BACKGROUND

When people suffer from some types of heart arrhythmias, the result may be that blood flow to various parts of the body is reduced. Some arrhythmias may even result in a Sudden Cardiac Arrest (SCA). SCA can lead to death very quickly, e.g. within 10 minutes, unless treated in the interim. Some observers have thought that SCA is the same as a heart attack, which it is not.

Some people have an increased risk of SCA. Such people include patients who have had a heart attack, or a prior SCA episode. A frequent recommendation for these people is to receive an Implantable Cardioverter Defibrillator (ICD). The ICD is surgically implanted in the chest, and continuously monitors the patient's electrocardiogram (ECG). If certain types of heart arrhythmias are detected, then the ICD delivers an electric shock through the heart.

As an alternative further precaution, people who have been identified to have an increased risk of an SCA are sometimes given a Wearable Cardioverter Defibrillator (WCD) system, to wear until the time that their ICD is implanted. Early versions of such systems were called wearable cardiac defibrillator systems. A WCD system typically includes a harness, vest, belt, or other garment that the patient is to wear around the chest. The WCD system further includes electronic components, such as a defibrillator and electrodes, coupled to the harness, vest, or other garment. When the patient wears the WCD system, the electrodes may make good electrical contact with the patient's skin, and therefore can help sense the patient's ECG. If a shockable heart arrhythmia is detected from the ECG, then the defibrillator delivers an appropriate electric shock through the patient's chest, and thus through the heart to convert the dangerously fast rhythm and thus save their life.

The subject matter discussed in this Background section is not necessarily prior art to the disclosure and should not be presumed so simply because it is presented in this section. Rather, the discussion of any subject matter in this Background section should be read in conjunction with the detailed description below as merely a full and complete disclosure of the novel concepts.

BRIEF SUMMARY

The present description provides instances of wearable cardioverter defibrillator (WCD) systems, storage media that may store programs, and methods, the use of which may help overcome problems and limitations of the prior art.

In embodiments, a wearable cardioverter defibrillator (WCD) system includes an electrode, a support structure configured to be worn by an ambulatory patient to maintain the sensing electrodes in contact with the patient's body, and an energy storage module configured to store a charge that can be discharged via the shocking electrodes to deliver an electric shock to the patient.

The WCD further includes a processor programmed to detect the existence of a plurality of conditions (or categories of conditions). The processor is further programmed to prioritize each of the plurality of detected conditions, and to issue an alert based at least in part on the priorities of any detected conditions. The processor may issue only the highest priority alert while suppressing lower priority alerts until the highest priority alert has been remedied.

These and other features and advantages of the claimed invention will become more readily apparent in view of the embodiments described and illustrated in this specification, namely in this written specification and the associated drawings.

DETAILED DESCRIPTION

The detailed description set forth below in connection with the appended drawings, where like numerals reference like elements, are intended as a description of various embodiments of the present disclosure and are not intended to represent the only embodiments. Each embodiment described in this disclosure is provided merely as an example or illustration and should not be construed as precluding other embodiments. The illustrative examples provided herein are not intended to be exhaustive or to limit the disclosure to the precise forms disclosed.

In the following description, specific details are set forth to provide a thorough understanding of exemplary embodiments of the present disclosure. It will be apparent to one skilled in the art, however, that the embodiments disclosed herein may be practiced without embodying all the specific details. In some instances, well-known process steps have not been described in detail in order not to unnecessarily obscure various aspects of the present disclosure. Further, it will be appreciated that embodiments of the present disclosure may employ any combination of features described herein.

Wearable Cardioverter Defibrillators (WCD) are worn by patients at risk for sudden cardiac arrest. When a patient wears a WCD, the WCD may issue alerts to inform the user of system detected events that require patient action or alert users/bystanders of detected physiological events. The alerts may relate to a device status, equipment, and physiologic alerts. If numerous, the alerts may confuse the patient as to which condition should be remedied first or at least before other conditions. If a patient becomes frequently bothered by the WCD or confused about using it, the patient may cease to wear the WCD, resulting in increased risk to the patient's health.

Embodiments of this disclosure are directed to a wearable cardioverter defibrillator ("WCD") system design in which a WCD implements an alert prioritization scheme to provide the patient with feedback in an order that is less likely to cause confusion. Different conditions (e.g., device status, equipment condition, or physiologic condition) are prioritized based on an analysis of severity of the condition and timeliness of user action needed. The prioritization scheme defines what alert, if any, is presented to the user by the WCD system as a result of various conditions. Generally stated, an alert for the highest priority condition currently detected is presented to the user and maintained until that condition either changes or becomes surpassed in the prioritization scheme.

The WCD system according to embodiments may protect a patient by electrically converting the patient's heart to a nonlethal rhythm if needed. Such a WCD system may have a number of components. These components can be provided separately as modules that can be interconnected, or can be combined with other components, and so on.

Figure 1:
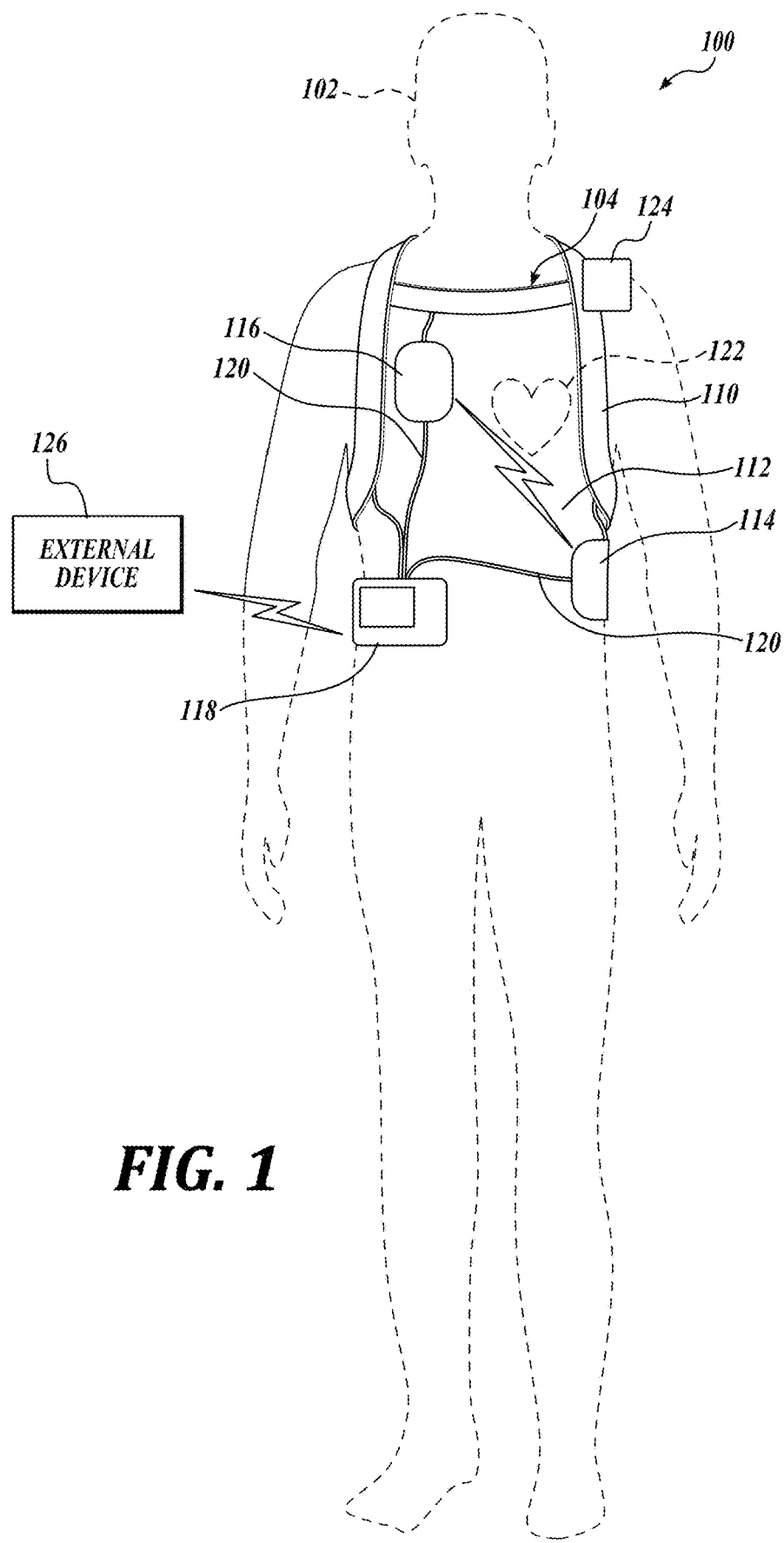
FIG. 1 is a diagram of components of a sample wearable cardioverter defibrillator (WCD) system, made according to embodiments.

FIG. 1 depicts a patient 82. Patient 82 may also be referred to as a person and/or wearer, since the patient is wearing components of the WCD system. Patient 82 is ambulatory, which means that, while wearing the wearable portion of the WCD system, patient 82 can walk around and is not necessarily bed-ridden. While patient 82 may be considered to be also a "user" of the WCD system, this is not a requirement. For instance, a user of the wearable cardioverter defibrillator (WCD) may also be a clinician such as a doctor, nurse, emergency medical technician (EMT) or other similarly tasked individual or group of individuals. In some cases, a user may even be a bystander. The particular context of these and other related terms within this description should be interpreted accordingly.

A WCD system according to embodiments can be configured to defibrillate the patient who is wearing the designated parts the WCD system. Defibrillating can be by the WCD system delivering an electrical charge to the patient's body in the form of an electric shock. The electric shock can be delivered in one or more pulses.

In particular, FIG. 1 also depicts components of a WCD system made according to embodiments. One such component is a support structure 170 that is wearable by ambulatory patient 82. Accordingly, support structure 170 is configured to be worn by ambulatory patient 82 for at least several hours per day, and for at least several days, even a few months. It will be understood that support structure 170 is shown only generically in FIG. 1, and in fact partly conceptually. FIG. 1 is provided merely to illustrate concepts about support structure 170 and is not to be construed as limiting how support structure 170 is implemented, or how it is worn.

Support structure 170 can be implemented in many different ways. For example, it can be implemented in a single component or a combination of multiple components. In embodiments, support structure 170 could include a vest, a half-vest, a garment, etc. In such embodiments such items can be worn similarly to analogous articles of clothing. In embodiments, support structure 170 could include a harness, one or more belts or straps, etc. In such embodiments, such items can be worn by the patient around the torso, hips, over the shoulder, etc. In embodiments, support structure 170 can include a container or housing, which can even be waterproof. In such embodiments, the support structure can be worn by being attached to the patient's body by adhesive material, for example as shown and described in U.S. Pat. No. 8,024,037. Support structure 170 can even be implemented as described for the support structure of US Pat. App. No. US2017/0056682, which is incorporated herein by reference. Of course, in such embodiments, the person skilled in the art will recognize that additional components of the WCD system can be in the housing of a support structure instead of being attached externally to the support structure, for example as described in the US2017/0056682 document. There can be other examples.

FIG. 1 shows a sample external defibrillator 100. As described in more detail later in this document, some aspects of external defibrillator 100 include a housing and an energy storage module within the housing. As such, in the context of a WCD system, defibrillator 100 is sometimes called a main electronics module. The energy storage module can be configured to store an electrical charge. Other components can cause at least some of the stored electrical charge to be discharged via electrodes through the patient, so as to deliver one or more defibrillation shocks through the patient.

FIG. 1 also shows sample defibrillation electrodes 104, 108, which are coupled to external defibrillator 100 via electrode leads 105. Defibrillation electrodes 104, 108 can be configured to be worn by patient 82 in a number of ways. For instance, defibrillator 100 and defibrillation electrodes 104, 108 can be coupled to support structure 170, directly or indirectly. In other words, support structure 170 can be configured to be worn by ambulatory patient 82 so as to maintain at least one of electrodes 104, 108 on the body of ambulatory patient 82, while patient 82 is moving around, etc. The electrode can be thus maintained on the body by being attached to the skin of patient 82, simply pressed against the skin directly or through garments, etc. In some embodiments the electrode is not necessarily pressed against the skin but becomes biased that way upon sensing a condition that could merit intervention by the WCD system. In addition, many of the components of defibrillator 100 can be considered coupled to support structure 170 directly, or indirectly via at least one of defibrillation electrodes 104, 108.

When defibrillation electrodes 104, 108 make good electrical contact with the body of patient 82, defibrillator 100 can administer, via electrodes 104, 108, a brief, strong electric pulse 111 through the body. Pulse 111 is also known as shock, defibrillation shock, therapy, electrotherapy, therapy shock, etc. Pulse 111 is intended to go through and restart heart 85, in an effort to save the life of patient 82. Pulse 111 can further include one or more pacing pulses of lesser magnitude to simply pace heart 85 if needed, and so on.

Sometimes a WCD system may diagnose incorrectly patient 82. In fact, such a WCD system may even administer defibrillation shock 111 as therapy to patient 82 when patient 82 does not need it, for instance when patient 82 is not having SCA, and is conscious. To prevent an undesirable shock 111 under such circumstances, a WCD system according to embodiments may further include a divert actuator 189 that is coupled to support structure 170 and configured to be actuated by patient 82. Divert actuator 189 is also known as cancel switch, "I am alive" switch, "live man" switch, therapy divert switch, and so on. As will be seen later in this document, divert actuator 189 is typically one more input device of an overall user interface 280.

In the shown embodiment, divert actuator 189 is a button in a stand-alone small housing 188 that has a wire 186. Wire 186 can, in turn, be ultimately electrically coupled with external defibrillator 100. In other embodiments, the divert actuator can be a lever, a switch, etc. In such embodiments, the WCD system may further have an output device configured to output an alarm, and permit patient 82 some time to actuate divert actuator 189 responsive to the alarm. If patient 82 does that within the permitted time, then patient 82 is not shocked.

In such embodiments, the WCD system may further include a tactile output device 184, for example within small housing 188. Device 184 can be configured to output a confirmation vibration, responsive to the divert actuator 189 being actuated. For example, responsive to patient 82 pushing button 189, a small motor can rotate briefly to produce the confirmation vibration.

The defibrillator may decide whether to defibrillate or not based on an ECG signal of the patient. However, external defibrillator 100 may initiate defibrillation, or hold-off defibrillation, based on a variety of inputs, with the ECG signal merely being one of these inputs.

A WCD system according to embodiments can obtain data from patient 82. For collecting such data, the WCD system may optionally include at least an outside monitoring device 180. Device 180 is called an "outside" device because it could be provided as a standalone device, for example not within the housing of defibrillator 100. Device 180 can be configured to sense or monitor at least one local parameter. A local parameter can be a parameter of patient 82, or a parameter of the WCD system, or a parameter of the environment, as will be described later in this document.

For some of these parameters, device 180 may include one or more sensors or transducers. Each one of such sensors can be configured to sense a parameter of patient 82, and to render an input responsive to the sensed parameter. In some embodiments the input is quantitative, such as values of a sensed parameter; in other embodiments the input is qualitative, such as informing whether or not a threshold is crossed, and so on. Sometimes these inputs about patient 82 are also called physiological inputs and patient inputs. In embodiments, a sensor can be construed more broadly, as encompassing many individual sensors.

Optionally, device 180 is physically coupled to support structure 170. In addition, device 180 may be communicatively coupled with other components that are coupled to support structure 170. Such communication can be implemented by a communication module, as will be deemed applicable by a person skilled in the art in view of this description.

In embodiments, one or more of the components of the shown WCD system may be customized for patient 82. This customization may include a number of aspects. For instance, support structure 170 can be fitted to the body of patient 82. For another instance, baseline physiological parameters of patient 82 can be measured, such as the heart rate of patient 82 while resting, while walking, motion detector outputs while walking, etc. The measured values of such baseline physiological parameters can be used to customize the WCD system, in order to make its diagnoses more accurate, since patients' bodies differ from one another. Of course, such parameter values can be stored in a memory of the WCD system, and so on. Moreover, a programming interface can be made according to embodiments, which receives such measured values of baseline physiological parameters. Such a programming interface may input automatically in the WCD system these, along with other data.

Figure 2:
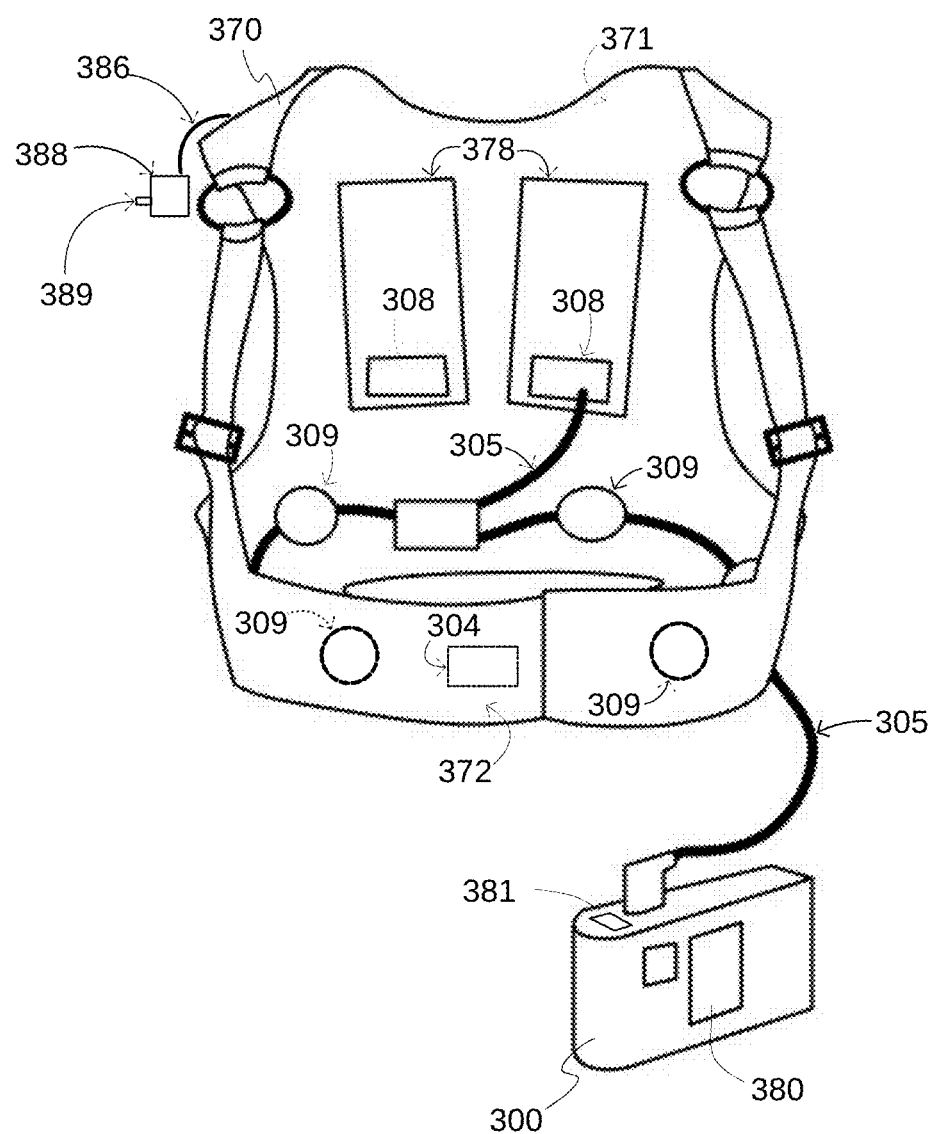
FIG. 2 is another diagram of a sample embodiment of a WCD system that may benefit from embodiments of the present disclosure.

FIG. 2 is another diagram of components of an illustrative WCD system. A support structure 370 includes a vest-like wearable garment. Support structure 370 has a back side 371 and a front side 372 that closes in front of the chest of the patient.

The WCD system of FIG. 2 also includes an external defibrillator 300. Although FIG. 3 does not show any support for external defibrillator 300, it may be attached to the support structure 370, carried on a belt, in a purse, by a strap over the shoulder, and so on. Wires 305 connect external defibrillator 300 to electrodes 304, 308, 309. Of those, electrodes 304, 308 are defibrillation electrodes, and electrodes 309 are ECG sensing electrodes. A therapy divert button 389 is provided on a small housing 388 which, in turn, is connected via a cable 386 to defibrillator 300, similarly to what was described with reference to FIG. 1.

Existing WCD systems use a large display screen facing away from the patient to convey information about the system state to the patient or to someone rendering aid. Existing display screens are large enough to provide information about concurrent system conditions and are in a prominent position at the front of the WCD electronics module. However, it is difficult for the patient to view the display screen of existing WCD systems while wearing the existing WCD system. In addition, display screens on existing WCD systems do not allow for discrete notifications of system conditions.

In contrast, embodiments of the present disclosure use a small display 380 and LED 381 along the outer edge of the electronics module 300. Positioning the LED 381 along the periphery of the electronics module 300 allows the patient to discretely review system conditions and alerts without handling the electronics module 300. Further, and in accordance with the disclosure, embodiments of the user interface design of the WCD system handle concurrent system conditions by prioritizing these conditions and providing user feedback based on those priorities.

In one implementation, the WCD system issues an alert only for the current condition having the highest priority. In other words, embodiments of the disclosed WCD user feedback scheme are simple and focused so the patient can easily identify and fix the most important issue as soon as possible. This prioritization scheme provides at least the following benefits: (1) The user is only informed of the most relevant condition, which allows the user to take quick and decisive action without confusion, and (2) there is a 1-to-1 relationship between content presented on the WCD display 380 or LED 381 and the expected action as explained to a user in a manual or guide; e.g. the user does not need to interpret multiple symbols and figure out which condition is more important to address.

Support structure 370 is configured to be worn by the ambulatory patient to maintain electrodes 304, 308, 309 on a body of the patient. Indeed, back defibrillation electrodes 308 are maintained in pockets 378. Of course, the inside of pockets 378 can be made with loose netting, so that electrodes 308 can contact the back of the patient, especially with the help of the conductive fluid that has been deployed. In addition, sensing electrodes 309 are maintained in positions that surround the patient's torso, for sensing ECG signals and/or the impedance of the patient.

Figure 3:
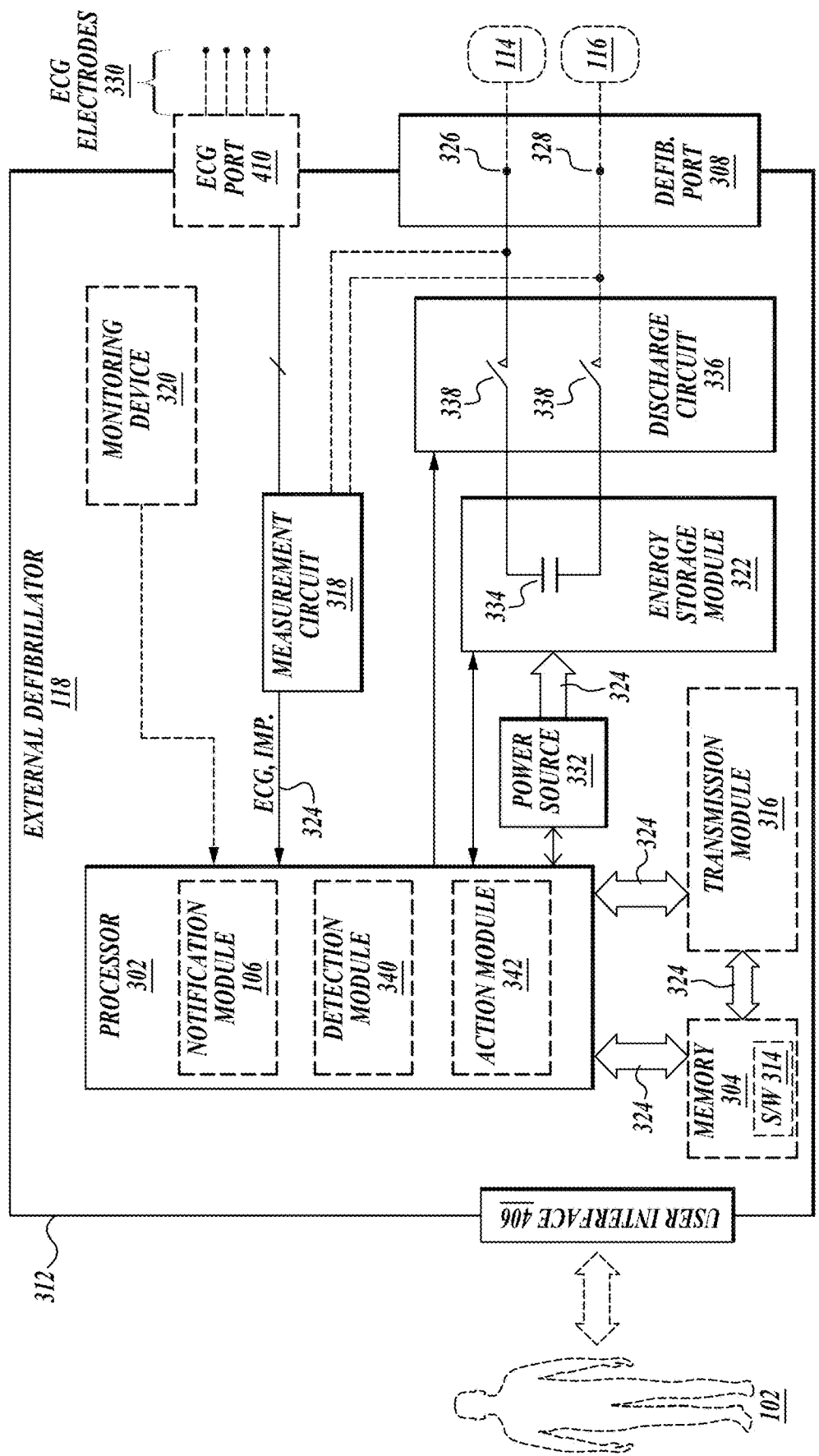
FIG. 3 is a block diagram showing sample components of an external defibrillator, such as the one used in the systems of FIGS. 1, and 2 and which is made according to embodiments.

FIG. 3 is a functional block diagram displaying various components of one example of a defibrillator 118 in accordance with the disclosure. The defibrillator 118 may be an example of the defibrillator 118 described with reference to FIG. 1. The components shown in FIG. 3 may be contained within a single unit or may be separated amongst two or more units in communication with each other. The defibrillator 118 may include a processor 302, memory 304, user interface 306, defibrillation port 308, ECG port 310, among other components. In some embodiments, the components are contained within a housing 312 or casing. The housing 312 may comprise a hard shell around the components or may comprise a softer shell for increased patient comfort.

The processor 302, memory 304 (including software/firmware code (SW) 314), user interface 306, defibrillation port 308, ECG port 310, transmission module 316, measurement circuit 318, monitoring device 320, and energy storage module 322 may communicate—directly or indirectly—with one another (e.g., via one or more buses 324). One or more buses 324 may allow data communication between one or more elements and/or modules of the defibrillator 118.

The memory 304 may include random access memory (RAM), read only memory (ROM), flash RAM, and/or other types. The memory 304 may store computer-readable, computer-executable software/firmware code 314 including instructions that, when executed, cause the processor 302 to perform various functions (e.g., determine shock criteria, determine consciousness of patient, track patient parameters, etc.). In some embodiments, the processor 302 may include an intelligent hardware device, e.g., a central processing unit (CPU), a microcontroller, an application-specific integrated circuit (ASIC), etc.

In some embodiments, the memory 304 can contain, among other things, the Basic Input-Output system (BIOS) which may control basic hardware and/or software operations such as interactions and workings of the various components of the defibrillator 118, and in some embodiments, components external to the defibrillator 118. For example, the memory 304 may contain various modules to implement the workings of the defibrillator 118 and other aspects of the present disclosure.

In some embodiments, the defibrillator 118 may include a user interface 306. The user interface 306 may enable the patient to view one or metrics concerning the defibrillator 118, the WCD system as a whole, or some combination thereof. For example, the user interface 306 may display an ECG of the patient, a status of the defibrillator 118, a status of a charge (e.g. a battery charge or an energy storage module), an alert to bring an unsafe condition to the patient's attention, and the like.

In some embodiments, the defibrillator 118 may include a defibrillation port 308. The defibrillation port 308 may comprise a socket, opening, or electrical connection in the housing 312. In some instances, the defibrillation port 308 may include two or more nodes 326, 328. The two or more nodes 326, 328 may accept two or more defibrillation electrodes (e.g. defibrillation electrodes 114, 116, FIG. 1). The nodes 326, 328 may provide an electrical connection between the defibrillation electrodes 114, 116 and the defibrillator 118. The defibrillation electrodes 114, 116 may plug into the two or more nodes 326, 328 via one or more leads (e.g. leads 120), or, in some instances, the defibrillation electrodes 114, 116 may be hardwired to the nodes 326, 328. Once an electrical connection is established between the defibrillation port 308 and the electrodes 114, 116, the defibrillator 118 may be able to deliver an electric shock to the patient.

In some embodiments, the defibrillator 118 may include an ECG port 310 in the housing 312. The ECG port 310 may accept one or more ECG electrodes 330 or ECG leads. In some instances, the ECG electrodes 330 sense a patient's ECG signal. For example, the ECG electrodes 330 may record electrical activity generated by the heart muscle depolarization. The ECG electrodes 330 may utilize 3-leads to 12-leads or multichannel ECG, or the like. The ECG electrodes 330 may connect with the patient's skin.

In some embodiments, the defibrillator 118 may include a measurement circuit 318. The measurement circuit 318 may be in communication with the ECG port 310. For example, the measurement circuit 318 may receive physiological signals from ECG port 310. The measurement circuit 318 may additionally or alternatively receive physiological signals via the defibrillation port 308 when defibrillation electrodes 114, 116 are attached to the patient. The measurement circuit 318 may determine a patient's ECG signal from a difference in voltage between the defibrillation electrodes 114, 116.

In some embodiments, the measurement circuit 318 may monitor the electrical connection between the defibrillation electrodes 114, 116 and the skin of the patient. For example, the measurement circuit 318 can detect impedance between the electrodes 114, 116. In some embodiments, the detected impedance may indicate the effective resistance of an electric circuit. An impedance calculation may, at least in part, determine when the electrodes 114, 116 have a good electrical connection with the patient's body.

In some embodiments, the defibrillator 118 may include an internal monitoring device 320 within the housing 312. The monitoring device 320 may monitor at least one system parameter as well as patient physiological parameters. System parameters may include a parameter of the WCD (e.g. WCD 104), defibrillator 118, environmental parameters, or the like. For instance, the system parameter may reflect whether the WCD is being worn correctly and is in good working condition. Patient physiological parameters may include the patient's ECG and its concomitant elements. In addition, the monitoring device 320 may monitor environmental conditions, such as whether the WCD system in moving, thereby indicating that the patient is conscious and ambulatory. Other parameters may also be monitored.

In some embodiments, a WCD (e.g. WCD 104) may include an internal monitoring device 320 and an external monitoring device. If both monitoring devices are present, the devices may collaborate to parse out specific parameters depending on position, location, and other factors. For example, the external monitoring device may monitor environmental parameters while the internal monitoring device 320 may monitor patient and system parameters.

In some embodiments, the defibrillator 118 may include a power source 332. The power source 332 may comprise a battery or battery pack, which may be rechargeable. In some instances, the power source 332 may comprise a series of different batteries to ensure the defibrillator 118 has power. For example, the power source 332 may include a series of rechargeable batteries as a prime power source and a series of non-rechargeable batteries as a secondary source. If the patient is proximate an AC power source, such as when sitting down, sleeping, or the like, the power source 332 may include an AC override wherein the power source 332 draws power from the AC source.

In some embodiments, the defibrillator 118 may include an energy storage module 322. The energy storage module 322 may store electrical energy in preparation or anticipation of providing a sudden discharge of electrical energy to the patient. In some embodiments, the energy storage module 322 may have its own power source and/or battery pack.

In other embodiments, the energy storage module 322 may pull power from the power source 332. In still further embodiments, the energy storage module 322 may include one or more capacitors 334. The one or more capacitors 334 may store an electrical charge, which may be administered to the patient. The processor 302 may be communicatively coupled to the energy storage module 322 to trigger the amount and timing of electrical energy to provide to the defibrillation port 308 and, subsequently, the patient.

In some embodiments, the defibrillator 118 may include a discharge circuit 336. The discharge circuit 336 may control the energy stored in the energy storage module 322. For example, the discharge circuit 336 may either electrical couple or decouple the energy storage module 322 to the defibrillation port 308. The discharge circuit 336 may be communicatively coupled to the processor 302 to control when the energy storage module 322 and the defibrillation port 308 should or should not be coupled to either administer or prevent a charge from emitting from the defibrillator 118. In some embodiments, the discharge circuit 336 may include one or more switches 338. The one or more switches 338 may include an H-bridge.

In some embodiments, the defibrillator 118 may include a transmission module 316. The transmission module 316 may establish one or more communication links with either local hardware and/or software to the WCD and defibrillator 118 or to remote hardwire separate from the WCD system. In some embodiments, the transmission module 316 may include one or more antennas, processors, and the like. The transmission module 316 may communicate wirelessly via radio frequency, electromagnetics, local area networks (LAN), wide area networks (WAN), virtual private networks (VPN), RFID, Bluetooth, cellular networks, and the like. The transmission module 316 may facilitate communication of data and commands such as patient data, episode information, therapy attempted, CPR performance, system data, environmental data, and so on.

In some embodiments, the processor 302 may execute one or more modules. For example, the processor 302 may execute a detection module 340 and/or an action module 342. The detection module 340 may be a logic device or algorithm to determine if any thresholds are exceeded which may require action of the defibrillator 118. For example, the detection module 340 may receive and interpret all the signals from the ECG port 310, the defibrillation port 308, the monitoring device 320, an external monitoring device, and the like. The detection module 340 may process the information to ensure the patient is conscious and healthy. If any parameter indicates the patient may be experiencing distress or indicating a cardiac episode, the detection module 340 may activate the action module 342.

The action module 342 may receive data from the detection module 340 and perform a series of actions. For example, an episode may merely be a loss of batter power at the power source 332 or the energy storage module 322, or one or more electrodes (e.g., ECG electrodes, defibrillation electrodes) may have lost connection. In such instances, the action module 342 may trigger an alert to the patient or to an outside source of the present situation. If an episode is a health risk, such as a cardiac event, the action module 342 may begin a series of steps. This may include issuing a warning to the patient, issuing a warning to a third party, priming the energy storage module 322 for defibrillation, releasing one or more conductive fluids proximate defibrillation electrodes 114, 116, and the like.

In further embodiments, the processor 302 may also execute the notification module 106. The notification module 106 may detect that certain parameters reveal that the WCD system is in an unsafe condition necessitating that an alert be raised to apprise the patient of that unsafe condition. The notification module 106 of preferred embodiments also categorizes each condition, determines what alert to issue to the patient, and when the alert is issued. The notification module 106 may also determine or receive data to determine when a condition has been remedied. Condition resolution may cause the notification module 106 to cease an alert, issue a resolution notice, or a combination thereof.

One illustrative process that may be implemented by the notification module 106 to prioritize and raise alerts for unsafe conditions will now be described in conjunction with FIG. 4.

Figure 4:
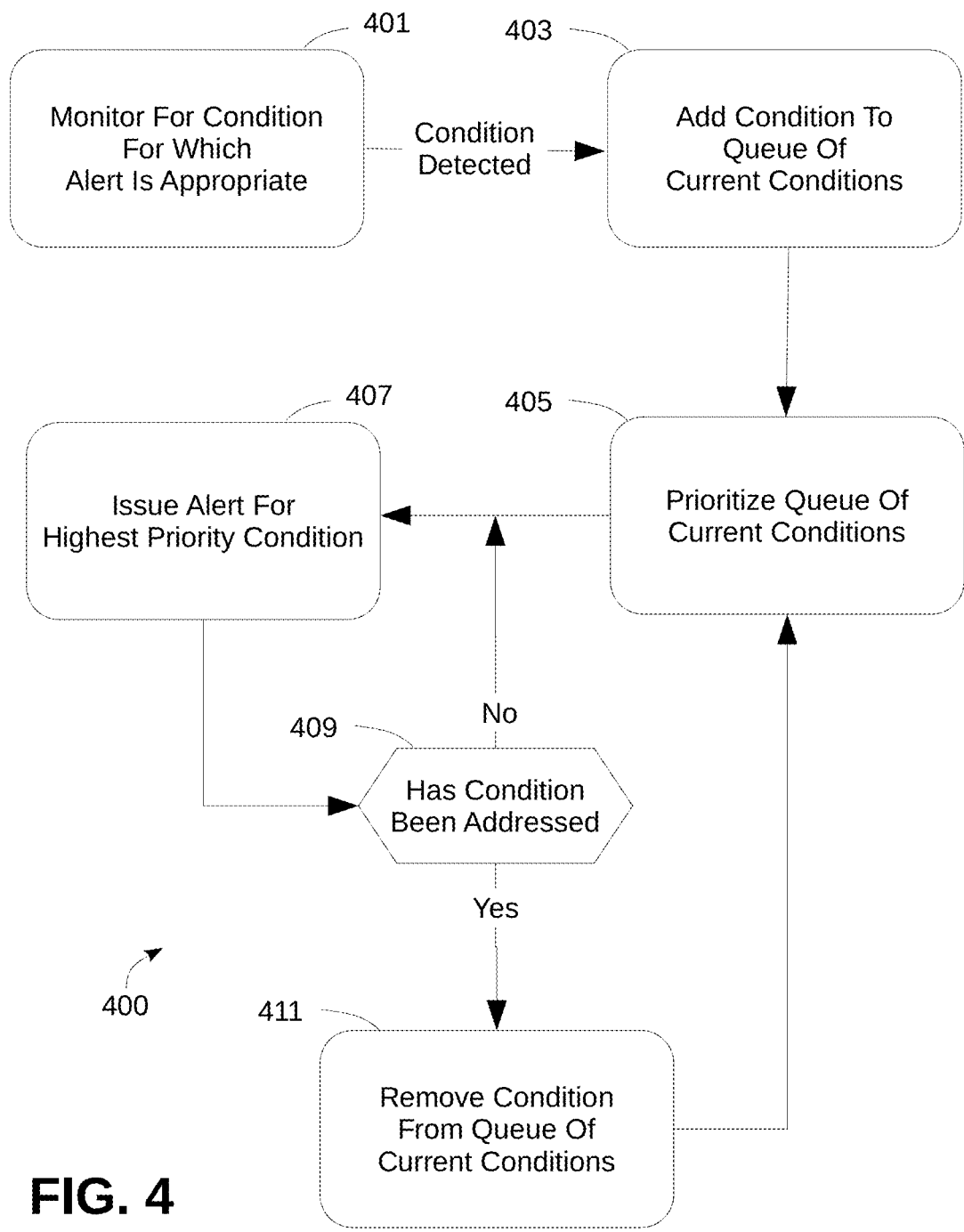
FIG. 4 is a functional flow diagram generally illustrating a process for prioritizing detected conditions for a WCD system.

FIG. 4 is a logical flow diagram generally illustrating a process 400 for prioritizing alerts in a WCD system in accordance with the disclosure.

At step 401, the process 400 monitors for a condition for which an alert is appropriate. As noted above, such a condition may represent either that some system parameter is outside of proper working conditions, or that some physiological condition with the patient may exist. Generally stated, each such condition indicates that action is either required or strongly recommended to return the WCD system to a safe and operable condition. For the purposes of this disclosure, the term "condition" means any unsafe condition of either the WCD system or the patient for which an action is either required or strongly recommended in order to return either the WCD system or the patient to a safe working order.

At step 403, when a condition is detected, the process adds that condition to a queue of current conditions. The queue of current conditions may be empty or it may include other conditions. It is envisioned that at system startup, the queue is empty. As system startup progresses, certain conditions may be promptly revealed (e.g., "the patient is not wearing the WCD" or the like) and added to the queue. In addition, as the WCD system is worn and used, other conditions may emerge and be added to the queue.

At step 405, as any new condition is added to the queue, the process 400 prioritizes each condition in the queue of current conditions. In various embodiments, the prioritization scheme used to prioritize each condition may weigh different parameters in different ways. However, generally stated, conditions that prevent the WCD from operating in its intended manner (e.g., the WCD is not being worn or has a critically low battery) are prioritized higher than conditions which should be remedied but which will still allow the WCD to function (e.g., the WCD has a low battery but not critically low).

Figure 5:
FIG. 5 is a table generally illustrating a condition prioritization scheme according to one embodiment of the present disclosure.

Turning briefly to FIG. 5, a table 500 illustrates one example prioritization scheme according to certain embodiments. This example prioritization scheme considers the Modes and States behavior of the WCD, the need to fix issues preventing cardiac sensing and/or treatment as soon as possible, and desire to inform the user of relevant, but not critical, system issues. Note that many of these conditions are possible concurrently. In contrast to existing systems that show multiple alerts or notifications at once, embodiments of the present disclosure only show one alert at a time to avoid confusing and/or stressing the patient. In embodiments, when multiple conditions occur, only the highest priority alert is provided, and when the patient resolves the issue, the next highest priority alert is provided, and so on.

Figure 6:
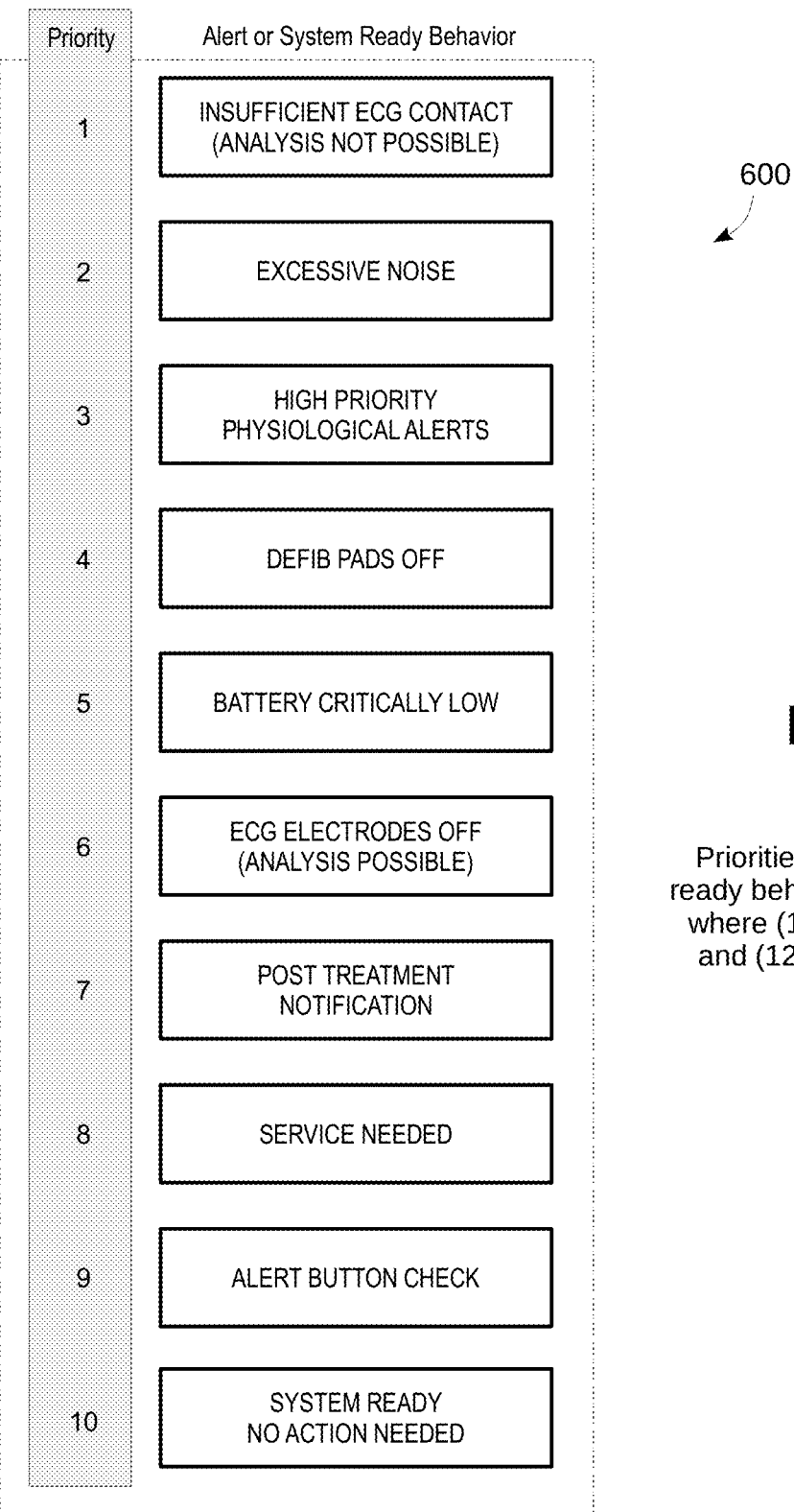
FIG. 6 is a table generally illustrating another condition prioritization scheme according to one embodiment of the present disclosure.

This example prioritization has some system conditions with higher priority than physiological condition, which may be counterintuitive compared to other WCD alert schemes. In another example prioritization, the alerts shown in FIG. 5 for priority 5 and priority 6 are switched as illustrated in FIG. 6.

There are many possible prioritization schemes used in embodiments, some of which could dynamically adjust the alert prioritization during operation of the WCD. Some examples of alert prioritization schemes, which can be combined as needed, are:

1. Type of Alert—Physiologic>Equipment>Device Status
2. Timeliness of Response Needed—Soon>sometime in the future; for example, Service Required and Service Needed require the same user action (get service) but have significantly different timeliness of response needed since Service Required means the WCD cannot deliver therapy.
3. Severity of No Response—Death>severe injury>harm
4. System Mode—Different priorities based on the current system mode; for example, prioritize alerts differently when in Holter Mode to allow for collection of data on what the system would do if an alert had not been issued.
5. System State—Different priorities based on the current system state; for example, prioritize alerts differently when Not Being Worn compared to Being Worn.
6. Sub-Category Prioritization—Different priorities based on the specific alert-causing reason; for example a prioritization scheme could be implemented to allow for a higher priority notification for Service Needed (Gel replenishment needed) than Service Needed (system component exceeded service life). An alert for Service Needed (system component exceeded expected service life) could even be prioritized lower than System Ready, No User Action Needed, which essentially turns the user-facing alert off but still logs the condition for device service or remote device management purposes.
7. Connected System Status—Different priorities based on the presence or absence of connected system components; for example, use different priorities if the WCD is currently connected to a portable "smart device" such as a tablet or a smartphone-like device. In some embodiments, the "smart device" is called an "Assistant" and includes wireless communication connectivity with the WCD's electronics module and can serve as a UI to the electronics module, as well as connect to a network to communicate with remote devices. For example, in some embodiments, clinicians, emergency responders, family members, monitoring services, etc. may be selectively connected to the WCD either directly or via the "Assistant" and receive information from the WCD, the user, and/or rescuers or bystanders. In some embodiments, the prioritization scheme for alerts provided to the remote devices may be different from the prioritization scheme for the user. For example, a "clinician view" may be implemented on a remotely connected device that uses a different prioritization, and in some cases displays 2 or more alerts concurrently as opposed to the single alert displayed on the WCD user's UI. In some embodiments, the clinician view may display alerts with a different timing (e.g., in real time) than the WCD's user's UI.
8. Time of Day—Different priorities based on time of day (see #9 below for a more likely use of this prioritization).
9. Time Since Entering Being Worn—Different priorities to allow for the device to acclimate to the user prior to alerting for poor contact issues.
10. Sleep Detection—Different priorities based on sleep detection; for example, if the defib pads are noticed to come off frequently while sleeping, this alert can be prioritized lower to prevent interrupting the patient's sleep.
11. User Input—Different priorities based on input from the user; for example, if the user informs the device that they are showering, the device can enter a "showering mode" in which a "Device Temporarily Not Being Worn" alert is prioritized higher than other Being Worn alerts.
12. Location—Different priorities based on location sensing; for example, if the device detects or the user informs the device that the user is in a "Public" setting, alerts could be prioritized to reduce or turn off the occurrence of certain alerts.
13. Manual—Different priorities based on manual customization on a patient-by-patient basis; for example, if a physician noticed that a patient frequently receives an alert that the physician feels does not affect the safety and efficacy of the WCD, like ECG Electrodes Off (Analysis Possible), and is concerned about patient compliance due to over-alerting, a user can program that alert to be lower priority than System Ready, No User Action Needed on the priority list, which essentially turns the user-facing alert off but still logs the condition for device service or remote device management purposes.

Returning to FIG. 4, because a condition for which an alert is appropriate has been detected, an alert is issued (step 407). The alert can take many forms, such as a visual icon or other notification rendered on a display, such as the display 380 or LED 381 (FIG. 2). In one preferred embodiment, an audible alert is also generated. The alert for the highest priority condition remains active until a higher priority condition is added to the queue. The process 400 continues monitoring these conditions (step 409) to constantly reassess which alert to raise for any current conditions. It will be appreciated that an important aspect of the alert prioritization schemes described above is the WCD system response to concurrent alert conditions. The following guidance describes design criteria that influence how to handle (e.g., prioritize) concurrent conditions, such as when new conditions are added to the queue.

1. Higher Priority Interruption of a Non-Physiologic Alert Condition—If a non-Physiologic Alert or system condition is active and a new, higher priority Alert occurs, the WCD will:
   i. Stop current user interface behavior of the active Alert or system condition (this includes any currently playing tactile and audio feedback).
   ii. Start the higher priority Alert or system condition behavior from the beginning.
2. Higher Priority Interruption of a Physiologic Alert—If a Physiologic Alert or system condition is active and a new, higher priority Alert occurs, the WCD shall:
   i. Stop current user interface behavior of the active Alert or system condition (this includes any currently playing tactile and audio feedback).
   ii. Skip any Onset Time and Initial Play Delay and start the higher priority Alert or system condition behavior.
3. Physiologic Alert Progression—If a Physiologic Alert is Active or Playing and the WCD advances to a new Physiologic state (i.e. advancing from Initial Patient Response Delay to Therapy Imminent), the WCD shall:

i. Stop current user interface behavior of the active Alert or system condition (this includes any currently playing tactile and audio feedback).

ii. Start the Alert behavior for the current State.

4. Lower Priority Occurrence During a Higher Priority Condition—If an Alert is active and a new, lower priority Alert occurs, the WCD shall:

i. Not interrupt the current (higher priority) Alert.

ii. If the lower priority condition still exists upon resolution of the current Alert, start the Alert behavior of the lower priority condition.

Although described here in the context of one preferred embodiment, other prioritization schemes or methods for handling new conditions will become apparent from the teachings of the present disclosure.

At step 411, when any condition (not only the highest-priority condition) has been remedied, it is removed from the queue. However, it should be noted that in one preferred embodiment, the alert may be temporarily paused (or "snoozed") to be dealt with later. However, in accordance with this preferred embodiment, the alert may not be dismissed until the condition has in fact been remedied. In an alternative embodiment, the alert may be dismissed even though the condition has not been remedied.

Embodiments of this disclosure overcome various problems that exist with other WCD alerting systems. For example, user confusion about what action is required due to over-informing of system condition (like flashing between system is ok and service needed or indicating system is ok with a service wrench) is reduced or eliminated.

In some embodiments, a WCD configured with the disclosed prioritization scheme also includes a mechanism to detect if the patient or user accidentally or mistakenly disabled an alert or alarm. For example, the device may be configured to detect when an alarm is deactivated or disabled and monitor for subsequent actions by the patient that indicate the deactivation was not intended (e.g., monitor the patient's voice via a microphone, monitor UI inputs that indicate the patient is trying to repeat the alarm, or the like), or prompt the patient to confirm that the deactivation was intended, or if no response or an improper response is provided within a certain period of time.

The above described embodiments are adapted for use in WCD systems, but other embodiments can be used with other medical devices that provide alerts to the patient such as, for example, wearable vital sign monitors, Holter monitors, wearable external pacers, or other medical devices that monitor a patient, provide an alert/notification to the patient and/or a remote device, provide prompts or requests for a user (patient and/or rescuer or bystander) response, and optionally provide a therapy or treatment to the patient.

The devices and/or systems mentioned in this document may perform functions, processes, acts, operations, actions and/or methods. These functions, processes, acts, operations, actions and/or methods may be implemented by one or more devices that include logic circuitry. A single such device can be alternately called a computer, and so on. It may be a standalone device or computer, such as a general-purpose computer, or part of a device that has and/or can perform one or more additional functions. The logic circuitry may include a processor and non-transitory computer-readable storage media, such as memories, of the type described elsewhere in this document. Often, for the sake of convenience only, it is preferred to implement and describe a program as various interconnected distinct software modules or features. These, along with data are individually and also collectively known as software. In some instances, software is combined with hardware, in a mix called firmware.

Moreover, methods and algorithms have been described above. These methods and algorithms are not necessarily inherently associated with any particular logic device or other apparatus. Rather, they are advantageously implemented by programs for use by a computing machine, such as a general-purpose computer, a special purpose computer, a microprocessor, a processor such as described elsewhere in this document, and so on.

This detailed description may include flowcharts, display images, algorithms, and symbolic representations of program operations within at least one computer readable medium. An economy may be achieved in that a single set of flowcharts can be used to describe both programs, and also methods. So, while flowcharts describe methods in terms of boxes, they may also concurrently describe programs.

In the methods described above, each operation can be performed as an affirmative act or operation of doing, or causing to happen, what is written that can take place. Such doing or causing to happen can be by the whole system or device, or just one or more components of it. It will be recognized that the methods and the operations may be implemented in a number of ways, including using systems, devices and implementations described above. In addition, the order of operations is not constrained to what is shown, and different orders may be possible according to different embodiments. Examples of such alternate orderings may include overlapping, interleaved, interrupted, reordered, incremental, preparatory, supplemental, simultaneous, reverse, or other variant orderings, unless context dictates otherwise. Moreover, in certain embodiments, new operations may be added, or individual operations may be modified or deleted. The added operations can be, for example, from what is mentioned while primarily describing a different system, apparatus, device or method.

A person skilled in the art will be able to practice the present invention in view of this description, which is to be taken as a whole. Details have been included to provide a thorough understanding. In other instances, well-known aspects have not been described, in order to not obscure unnecessarily this description.

Some technologies or techniques described in this document may be known. Even then, however, it does not necessarily follow that it is known to apply such technologies or techniques as described in this document, or for the purposes described in this document.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases "constructed to", "adapted to" and/or "configured to" denote one or more actual states of construction, adaptation and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Incorporation by reference: References and citations to other documents, such as patents, patent applications, patent publications, journals, books, papers, web contents, have been made throughout this disclosure. All such documents are hereby incorporated herein by reference in their entirety for all purposes.

Parent patent applications: Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

Reference numerals: In this description a single reference numeral may be used consistently to denote a single item, aspect, component, or process. Moreover, a further effort may have been made in the preparation of this description to use similar though not identical reference numerals to denote other versions or embodiments of an item, aspect, component or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

The claims of this document define certain combinations and subcombinations of elements, features and acts or operations, which are regarded as novel and non-obvious. The claims also include elements, features and acts or operations that are equivalent to what is explicitly mentioned. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that the claim can have one or more of that component or that item.

In construing the claims of this document, the inventor(s) invoke 35 U.S.C. § 112(f) only when the words "means for" or "steps for" are expressly used in the claims. Accordingly, if these words are not used in a claim, then that claim is not intended to be construed by the inventor(s) in accordance with 35 U.S.C. § 112(f).

What is claimed is:

1. A wearable cardioverter defibrillator (WCD) system for a patient, comprising:
    an electrode;
    a support structure configured to be worn by the patient so as to maintain the electrode on the patient;
    an energy storage module configured to store an electrical charge that can be discharged via the electrode so as to deliver a shock to the patient when an ECG signal indicates that treatment is warranted;
    one or more sensors configured to detect a plurality of conditions wherein the plurality of conditions comprises at least a condition of whether the electrode is in sufficient contact with the patient and whether the WCD is in need of service; and
    a processor configured to:
        prioritize each condition in the plurality of conditions based on an analysis of a severity of each condition and a timeliness of remedying action needed,
        issue a first alert corresponding to a highest priority condition in the plurality of conditions, wherein if the electrode is not in sufficient contact with the patient and the WCD is in need of service, the condition that the electrode is not in sufficient contact with the patient is a higher priority than the condition that the WCD is in need of service; and
        defer any other alert for any other condition in the plurality of conditions until the highest priority condition has been remedied.

2. The WCD system recited in claim 1, wherein the WCD further comprises a display screen upon which the alert is shown.

3. The WCD system recited in claim 2, wherein the display screen is located on a periphery of an electronics module of the WCD such that the display screen is visible to the patient when the WCD is being worn.

4. The WCD system recited in claim 1, wherein the display screen shows only the first alert of a plurality of possible alerts wherein each of the plurality of possible alerts corresponds to a respective condition in the plurality of conditions.

5. The WCD system recited in claim 1, wherein the sensors detect physiological parameters and system parameters, the physiological parameters comprising information about the patient's vital statistics, and the system parameters comprising information about the WCD other than the patient's vital statistics.

6. The WCD system recited in claim 5, wherein the sensors further monitor environmental conditions, the environmental conditions including a movement of the WCD system.

7. The WCD system recited in claim 1, wherein the processor is further configured to issue a second alert upon a determination that the first alert has been remedied.

8. The WCD system recited in claim 7, wherein the second alert is issued after another analysis of a current plurality of conditions identified by the sensors after the first alert has been remedied and another analysis of the severity of each condition and the timeliness of remedying action needed for each condition in the current plurality of conditions.

9. The WCD system recited in claim 1, wherein the processor is further configured to issue a second alert upon a determination that a new condition has a higher priority than the condition corresponding to the first alert.

10. The WCD system recited in claim 1, wherein the plurality of conditions comprises a queue of conditions identified by the sensors, each condition being associated with a state of either a system parameter or a physiological parameter, the system parameter being associated with either the WCD or the environment in which the WCD operates, the physiological parameter being associated with vital statistics of the patient.

11. The WCD system recited in claim 1, wherein the plurality of conditions further comprises a condition whether service of the WCD is required before the WCD can be placed in operation, and further wherein the condition that service of the WCD is required is a higher priority than the condition that the electrode is not in sufficient contact with the patient.

12. The WCD system recited in claim 1, wherein the configuration to detect a plurality of conditions comprises a configuration to identify an indication of a condition of the plurality of conditions.

13. The WCD system recited in claim 1, wherein the processor is further configured to determine when the ECG signal indicates that treatment is warranted by:

receiving the ECG signal from an ECG sensor; and
analyzing the ECG signal to detect a shockable heart arrhythmia.

14. The WCD system recited in claim 13, wherein in response to the detection of the shockable heart arrythmia, the processor causes the energy storage module to discharge the electrical charge via the electrode to deliver a shock to the patient.

15. The WCD system recited in claim 13, wherein the electrode comprises the ECG sensor.

16. The WCD system recited in claim 13, wherein the display screen shows only the first alert of a plurality of possible alerts wherein each of the plurality of possible alerts corresponds to the condition in a plurality of conditions.

17. The WCD system recited in claim 13, wherein the processor is further configured to issue a second alert upon a determination that the first alert has been remedied.

18. The WCD system recited in claim 13, wherein the plurality of conditions further comprises a condition whether service of the WCD is required before the WCD can be placed in operation, and further wherein the condition that service of the WCD is required is a higher priority than the condition that the electrode is not in sufficient contact with the patient.

* * * * *

UNITED STATES PATENT AND TRADEMARK OFFICE
CERTIFICATE OF CORRECTION

PATENT NO. : 11,334,826 B2  
APPLICATION NO. : 16/748621  
DATED : May 17, 2022  
INVENTOR(S) : Z. Engman et al.

Page 1 of 1

It is certified that error appears in the above-identified patent and that said Letters Patent is hereby corrected as shown below:

In the Claims

| Column | Line | |
|--------|------|---|
| 18 | 5 | change "arrythmia" to -- arrhythmia --. |

Signed and Sealed this  
Thirteenth Day of September, 2022

Katherine Kelly Vidal  
*Director of the United States Patent and Trademark Office*